United States Patent [19]

Empfield et al.

[11] Patent Number: 5,693,639
[45] Date of Patent: Dec. 2, 1997

[54] THERAPEUTIC HETEROCYCLYL AMIONOSULFONYL PHENYL COMPOUNDS

[75] Inventors: James Roy Empfield, Bear, Del.; Daniel Ray Mayhugh, Indianapolis, Ind.; Keith Russell, Newark, Del.

[73] Assignee: Zeneca Limited, London, England

[21] Appl. No.: 604,064

[22] Filed: Feb. 20, 1996

Related U.S. Application Data

[62] Division of Ser. No. 212,456, Mar. 11, 1994, Pat. No. 5,510,386.

[30] Foreign Application Priority Data

May 17, 1993 [GB] United Kingdom ............... 9310095

[51] Int. Cl.$^6$ .................. A61K 31/54; A61K 31/535; C07D 401/02; C07D 249/12
[52] U.S. Cl. .................. 514/227.5; 514/238.2; 514/238.8; 514/317; 514/331; 514/424; 544/59; 544/158; 546/240; 546/264; 546/312; 548/542
[58] Field of Search ................. 544/59, 158; 546/240, 546/264, 312; 548/542

[56] References Cited

U.S. PATENT DOCUMENTS

| | | | |
|---|---|---|---|
| 3,291,837 | 12/1966 | Goldberg et al. | 250/591 |
| 3,365,485 | 1/1968 | Bell | 260/490 |
| 3,468,878 | 9/1969 | Bell | 260/239.3 |
| 3,661,917 | 5/1972 | Kaiser et al. | 260/293.73 |
| 3,662,071 | 5/1972 | Langkammerer. | |
| 3,715,375 | 2/1973 | Shen et al. | 424/275 |
| 3,885,047 | 5/1975 | Seidehamel et al. | 260/397.6 |
| 3,998,890 | 12/1976 | Glen | 424/330 |
| 4,239,776 | 12/1980 | Glen | 244/309 F |
| 4,282,218 | 8/1981 | Glen et al. | 424/304 |
| 4,330,542 | 5/1982 | Descamps et al. | 424/248.5 |
| 4,386,080 | 5/1983 | Crossley et al. | 424/207 |
| 4,535,092 | 8/1985 | Hughes | 514/438 |
| 4,636,505 | 1/1987 | Tucker | 514/254 |
| 4,845,119 | 7/1989 | Hughes et al. | 514/450 |
| 4,873,329 | 10/1989 | Hughes et al. | 514/265 |
| 4,880,839 | 11/1989 | Tucker | 514/613 |
| 5,032,592 | 7/1991 | Hughes et al. | 514/254 |
| 5,266,589 | 11/1993 | Van Dasler et al. | 514/438 |
| 5,272,163 | 12/1993 | Russell et al. | 514/317 |
| 5,403,930 | 4/1995 | Agback et al. | 544/235 |
| 5,474,999 | 12/1995 | Russell et al. | 514/256 |

FOREIGN PATENT DOCUMENTS

| | | |
|---|---|---|
| 2 020 971 | 1/1991 | Canada. |
| 0 181 568 | 5/1986 | European Pat. Off.. |
| 0 189 142 | 7/1986 | European Pat. Off.. |
| 0 253 503 | 1/1988 | European Pat. Off.. |
| 0 274 867 | 7/1988 | European Pat. Off.. |
| 0 382 368 | 8/1990 | European Pat. Off.. |
| 0 409 413 | 1/1991 | European Pat. Off.. |
| 0 409 414 | 1/1991 | European Pat. Off.. |
| 0 524 781 | 1/1993 | European Pat. Off.. |
| 7008627-Q | 6/1969 | Netherlands. |
| 7008629-Q | 6/1969 | Netherlands. |
| WO 93/23358 | 11/1993 | WIPO. |

OTHER PUBLICATIONS

R Bayles et al., "The Smiles rearrangement of 2–aryloxy–2–methylpropanamides. Synthesis of N–aryl–2–hydroxy–2–methylpropanamides" *Synthesis.* (1977), 31–33.

G Edwards et al., "Structure–activity relationships of potassium channel openers", *Trends in Pharmacological Sciences.* (1990), 11, 417–442.

B. Delfort, et al. "Ethynyl–Terminated Polyethers from New End–Capping Agents: Synthesis and Characterization" *Journal of Polymer Science: Part A: Polymer Chemistry* (1990), 28 (9), 2451–64.

Sandoz Ltd, Chemical Abstracts vol. 52, No. 5, col. 52:4194 through 52:4195, 1958.

Jackman et al, Chemical Abstracts vol. 55, No. 9, cols. 55:8335 through 55:8338, 1961.

J.J. Morris, et al. "Non–Steroidal Antiandrogens. Design of Novel Compounds Based on an Infrared Study of the Dominant Conformations and Hydrogen–Bonding Properties of a Series of Anilide Antiandrogens" *J. Med. Chem.* (1991), 34, 447–455.

S. Sarel, et al. "Factors Affecting Base–Induced Rearrangements of α–Chloro–α–,α–diphenylacetamides" *Journal of Organic Chemistry* (1970), 35(6), 1850–1857.

Jackman, et al. "The Condensation of Some Halogeno–2, 4–Disulphamyl–Benzene Derivatives with Basic Reagents" *Journal of Pharm. Pharmacol.* (1960), 12, 648–655.

*Primary Examiner*—Matthew V. Grumbling
*Attorney, Agent, or Firm*—Liza D. Hohenschutz

[57] ABSTRACT

Compounds of formula I

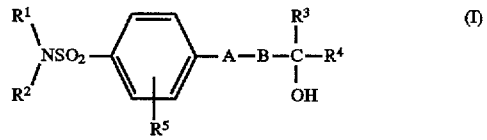

wherein $R^1$, $R^2$, $R^3$, $R^4$, $R^5$ and A-B have any of the meanings given in the specification, and their pharmaceutically acceptable salts are useful in the treatment of urinery incontinence. Also disclosed are pharmaceutical compositions, processes for preparing the compounds of formula I and intermediates.

9 Claims, No Drawings

THERAPEUTIC HETEROCYCLYL AMIONOSULFONYL PHENYL COMPOUNDS

This is a divisional application of application Ser. No. 08/212,456 filed on Mar. 11, 1994 now U.S. Pat. No. 5,510,386.

This invention relates to a novel group of compounds which are useful in the treatment of bladder instability in mammals such as man. More specifically, this invention relates to this group of compounds, their use in the treatment of urinary incontinence in mammals (including man), processes for preparing them and pharmaceutical compositions containing them.

It is known that bladder tissue is excitable and that urinary incontinence can be caused by uncontrolled or unstable bladder contractions. A group of compounds have been found that are unexpectedly capable of relaxing bladder smooth muscle, thus preventing or ameliorating uncontrolled or unstable bladder contractions. Hence, the compounds may be useful for the treatment of urge incontinence, which includes for example detrusor instability, which may result from cystitis, urethritis, tumors, stones, diverticuli or outflow obstruction; and detrusor hyperreflexia, which may result from stroke, dementia, Parkinsons, suprasacral spinalcord injury or suprasacral spinalcord disease.

This invention provides a compound of formula I (formula set out, together with other formulae referred to by Roman numerals, on pages following the Examples), wherein:

either $R^1$ and $R^2$ are each selected independently from hydrogen, (1–3 C)alkyl, pyridyl and phenyl which is unsubstituted or substituted by one or two substituents selected independently from (1–4 C)alkyl, (1–4 C)alkoxy, (2–4 C)alkenyloxy, hydroxy, halo and cyano, or $R^1$ and $R^2$ together with the nitrogen atom to which they are attached form morpholino, thiomorpholino, piperidinyl, pyrrolidinyl or imidazolyl;

A-B is selected from NHCO, $OCH_2$, $SCH_2$, $NHCH_2$, trans-vinylene, and ethynylene;

$R^3$ and $R^4$ are independently (1–3 C)alkyl substituted by from 0 to 2 k+1 atoms selected from fluoro and chloro wherein k is the number of carbon atoms in the said (1–3 C)alkyl, provided that $R^3$ and $R^4$ are not both methyl; or $R^3$ and $R^4$, together with the carbon atom to which they are attached, form a 3–5 membered cycloalkyl ring optionally substituted by from 0 to 2m-2 fluorine atoms wherein m is the number of carbon atoms in said ring; and $R^5$ is hydrogen, (1–4 C)alkyl, (1–4 C)haloalkyl, (1–4 C)alkoxy, (1–4)haloalkoxy, cyano, nitro, (2–4 C)alkenyloxy or trifluoromethylthio;

or a pharmaceutically acceptable in vivo hydrolyzable ester of said compound of formula I; or a pharmaceutically acceptable salt of said compound or said ester;

provided the compound is not 3-hydroxy-3-methyl-1-(4-morpholinosulfonylphenyl)-4,4,4-trifluorobut-1-yne.

The invention further provides a method for the treatment of urinary incontinence, comprising administering to a mammal (including man) in need of such treatment an effective amount of a sulphonamide of formula I as defined above, or a pharmaceutically acceptable in vivo hydrolyzable ester of said compound of formula I or a pharmaceutically acceptable salt of said compound or said ester.

The invention further provides a pharmaceutical composition comprising a sulphonamide of formula I as defined above, or a pharmaceutically acceptable in vivo hydrolyzable ester of said compound of formula I or a pharmaceutically acceptable salt of said compound or said ester, and a pharmaceutically acceptable diluent or carrier.

In this specification the terms "alkyl" and "alkoxy" include both straight and branched chain radicals, but it is to be understood that references to individual radicals such as "propyl" or "propoxy" embrace only the straight chain ("normal") radical, branched chain isomers such as "isopropyl" or "isopropoxy" being referred to specifically.

The term "halo" is inclusive of fluoro, chloro, bromo, and iodo unless noted otherwise.

It will be appreciated by those skilled in the art that certain compounds of formula I contain an asymmetrically substituted carbon and/or sulfur atom, and accordingly may exist in, and be isolated in, optically-active and racemic forms. Some compounds may exhibit polymorphism. It is to be understood that the present invention encompasses any racemic, optically-active, polymorphic or stereoisomeric form, or mixtures thereof, which form possesses properties useful in the treatment of urinary incontinence, it being well known in the art how to prepare optically-active forms (for example, by resolution of the racemic form by recrystallization techniques, by synthesis from optically-active starting materials, by chiral synthesis, or by chromatographic separation using a chiral stationary phase) and how to determine efficacy for the treatment of urinary incontinence by the standard tests described hereinafter.

Particular values for $R^1$ and $R^2$ when either group represents a (1–3 C)alkyl group are methyl, ethyl and propyl.

Particular values for substituents on phenyl when $R^1$ or $R^2$ represents substituted phenyl are methyl, ethyl, methoxy, ethoxy, allyloxy, hydroxy, fluoro, chloro, bromo and cyano.

Preferably either $R^1$ and $R^2$ are selected independently from hydrogen, methyl ethyl, propyl and phenyl, or $R^1$ and $R^2$ together with the nitrogen to which they are attached from morpholino, thiomorpholino, piperidinyl or pyrolidinyl.

Preferably either $R^3$ and $R^4$ both represent difluoromethyl, or $R^4$ represents trifluoromethyl and $R^3$ represents methyl or fluoromethyl. More particularly, $R^4$ represents trifluoromethyl and $R^3$ represents methyl.

Particular values of $R^5$ are hydrogen, methyl, ethyl, trifluoromethyl, methoxy, ethoxy, trifluoromethoxy, cyano, nitro, allyloxy and trifluoromethylthio. Preferably $R^5$ is hydrogen.

Preferably A-B represent NHCO, $OCH_2$, trans-vinylene or ethynylene. Most preferably it represents NHCO, trans-vinylene or ethynylene.

Compounds of formula I wherein A-B is NHCO represent a preferred embodiment of the invention.

A compound of formula I can be made by processes which include processes known in the chemical arts for the production of structurally analogous compounds. Such processes are provided as further features of the invention and are illustrated by the following procedures in which the meanings of generic radicals are as given above unless otherwise qualified. Such a process can be effected, generally, (a) by deprotecting a protected compound of formula II wherein "Pg" is a suitable alcohol protecting group, such as for example a benzyl group or a silyl protecting group; Examples of suitable reagents for deprotecting an amide of formula II when Pg is benzyl are (1) hydrogen in the presence of palladium-on-carbon catalyst, i.e. hydrogenolysis; or (2) hydrogen bromide or iodide; and when PG is a silyl protecting group are (1) tetrabutylammonium fluoride; or (2) aqueous hydrofluoric acid. The reaction can be conducted in a suitable solvent such as ethanol, methanol, acetonitrile, or dimethylsulfoxide and may conveniently be performed at a temperature in the range of −40° to 100° C.

(b) for a compound of formula I in which A-B is NHCO, by coupling an aniline of formula III with an acid of formula IV. The reaction can be conducted in a suitable solvent and in the presence of a suitable coupling reagent. Suitable coupling reagents generally known in the the art as standard peptide coupling reagents can be employed, for example thionyl chloride, carbonyldiimidazole and dicyclohexylcarbodiimide, optionally in the presence of a catalyst such as dimethylaminopyridine or 4-pyrrolidinopyridine. Suitable solvents include dimethylacetamide, dichloromethane, benzene, tetrahydrofuran, and dimethylformamide. The coupling reaction may conveniently be performed at a temperature in the range of −40° to 40° C.;

(c) for a compound of formula I in which A-B is ethynylene, by reacting a corresponding alkyne of formula V with a base such as lithium diisopropylamide (LDA), n-butyllithium or tert-butyllithium, followed by treatment with a ketone of formula $R^3$—CO—$R^4$. The reaction may conveniently be performed at a temperature in the range of −100° to −40° C. preferrably at a temperature in the range of −70° to −40° C. and in a solvent such as tetrahydrofuran (THF), diethyl ether, or 1,2-dimethoxyethane (DME).

(d) for a compound of formula I in which A-B is trans-vinylene, by reducing a corresponding compound of formula I in which A-B is ethynylene with a suitable reducing agent, for example lithium aluminum hydride or sodium bis(methoxyethoxy)aluminium hydride. The reaction can be conducted in a suitable solvent such as THF or diethyl ether, and at a temperature in the range of 0° to 50° C.

(e) for a compound of formula I in which A-B is tran-vinylene, by dehydration of a diol of formula VI in the presence of an acid catalyst (for example p-toluenesulfonic acid), neat or with a solvent such as toluene or dichloromethane, or a strong base (for example sodium hydride) in a solvent such as tetrahydrofuran and at a temperature in the range of 0° to 200° C. preferably a temperature in the range of 20° to 100° C.

(f) for a compound of formula I in which A-B is trans-vinylene, by base catalyzed opening of an epoxide of formula VII. The opening may be carried out in a suitable organic solvent such as for example, ethers, alcohols, or toluene; ethers such as tetrahydrofuran are preferred. Suitable bases include for example sodium hydroxide, sodium methoxide, potassium tert-butoxide or sodium hydride. A basic aqueous solution may conveniently be employed. A preferred base is aqueous sodium hydroxide. The opening may be carried out at a temperature in the range of −50° C. to 100° C., preferably at a temperature in the range of 0° to 50° C., such as for example room temperature.

(g) for a compound of formula I in which A-B is $NHCH_2$, by reducing a corresponding compound of formula I in which A-B is NHCO, with a suitable reducing agent such as lithium aluminum hydride or borane. The reaction can conveniently be carried out at a temperature in the range of 0° C. to reflux, in solvents such as for example diethyl ether, THF, or DME.

(h) for a compound of formula I in which A-B is $OCH_2$ or $SCH_2$, by reacting an ethylene oxide of formula VIII with a corresponding compound of formula IX (wherein J is, correspondingly, oxygen or sulfur), in the presence of a base such as for example sodium hydride. The reaction can be conducted at reflux in a solvent such as methylene dichloride.

(i) by reacting a compound of formula X in which Z is a leaving atom or group, for example a halogen atom such as fluoro or chloro, with an amine of formula $R^1R^2NH$. The reaction is conveniently performed in the presence of a base, for example a tertiary amine such as dimethylaminopyridine. Suitable solvents for the reaction include nitriles such as acetonitrile and amides such as dimethylformamide. The reaction is conveniently performed at a temperature in the range of from 0° to 120° C.

If not commercially available, the necessary starting materials for the procedures such as that described above may be made by procedures which are selected from standard organic chemical techniques, techniques which are analogous to the synthesis of known, structurally similar compounds, or techniques which are analogous to the above described procedure or the procedures described in the examples.

In general, a compound of formula II in which A-B is $OCH_2$, $SCH_2$ or $NHCH_2$ may be made by treating a corresponding compound of formula IX wherein J is oxygen, sulfur or NH with a corresponding compound of formula XI (wherein Pr is a protective group such as silyl and X is a suitable leaving group such as for example mesylate or triflate), in the presence of a base such as an alkali metal hydride (e.g., sodium hydride), in a solvent such as THF, DMF, DMSO, or DMPU, and at a temperature of about 20° C. to abut reflux. A compound of formulae II, wherein A-B is NHCO, may be made in a manner analogous to that described in procedure (b) above; that is, by coupling a corresponding aniline with a corresponding acid. The protected acid may be made by a conventional procedure, for example by (i) esterifying an acid of formula IV by means of a conventional esterification procedure such as reaction with a lower alcohol (e.g., methanol) in the presence of an acid catalyst (for example sulfuric acid); (ii) reaction of the ester thus formed with an agent which provides the protecting group Pg, such as benzyl chloride (to provide a benzyl protecting group) or any of the conventional silylating agents known and used for such purpose (such as 2-trimethylsilylethoxymethyl chloride, SEM, in the presence of a suitable base such as sodium hydroxide or triethylamine optionally in the presence of a catalyst such as DMAP); and (iii) cleavage of the ester group under mild alkaline conditions (i.e., employing a base such as potassium carbonate) to yield the desired protected acid.

A compound of formula V may be made by reacting a corresponding compound of formula XII, wherein L is bromo or iodo, with trimethylsilylacetylene in the presence of a catalyst such as a combination of bis (triphenylphosphine)palladium dichloride and copper(I) iodide in diethylamine or triethylamine, followed by treatment with a base (for example, an alkali metal hydroxide such as sodium or lithium hydroxide) in a lower alcohol as solvent to effect removal of the trimethylsilyl group.

A compound of formula VIII may be made by treating a corresponding ketone having the formula $R^3$—CO—$R^4$ with the ylide derived from the reaction of a trimethylsulfonium salt (such as trimethylsulfonium iodide) with a base (such as an alkali metal hydroxide). The reaction may be conducted in a one-pot process employing a solvent such as dichloromethane.

A compound of formula IX, wherein J is oxy, may be made by diazotizing a corresponding aniline of formula XII, wherein L is amino, as previously discussed, and heating in dilute sulfuric acid to form the corresponding phenol. The corresponding thiophenol may be formed by reacting an excess of methanethiol in the presence of sodium hydride with a corresponding compound of formula IX wherein L is a leaving group such as for example chloro.

A compound of formula X, in which A-B is NHCO may be prepared by coupling a compound of formula XIV with a compound of formula IV, following a method analogous to that of process (b) above.

A compound of formula XI, wherein X is mesylate, may be made by (1) esterifying an acid of formula IV; (2) protecting the alcohol group, by treating with for example trimethylsilyl chloride in a solvent such as dichloromethane and at a temperature of from about −78° to about 25° C.; (3) treating the protected compound thus obtained with a suitable reducing agent such as lithium aluminum hydride in a solvent such as diethyl ether or THF and at a temperature of about 0° to about 25° C., thereby reducing the carbonyl group to methylene; followed by (4) treating the reduced product with trifluoromethylsulfonic anhydride in the presence of a base such as triethylamine, in a solvent such as dichloromethane, and at a temperature of about −78° C. to about 25° C.

An epoxide of formula VII may be prepared from a diol of formula VI using a suitable dehydrating agent, for example bis[α,α-bis(trifluoromethyl)benzenemethanolato]diphenylsulphur.

A diol of formula VI may be prepared from a compound of formula I, wherein A-B is CHCO, by reduction. The reduction may be carried out using a suitable reducing agent, for example a hydride, such as sodium borohydride.

A compound of formula I, wherein A-B is CHCO, may be prepared from a compound of formula XII, wherein L is methyl, by deprotonation and treatment with an amide of formula XIII, in which $R^6$ and $R^7$ are each independently lower alkyl, or in which $R^6$ and $R^7$ when taken together with the atoms to which they are attached form a 5–7 membered ring. The deprotonation of the toluene may be carried out with a suitable base, for example lithium diisopropyl amide. The reaction may be carried out in a suitable organic solvent, for example, an ether such as tetrahydrofuran. The reaction may be carried out at a suitable temperature, for example a temperature in the range of −78° C. to 100° C.

An amide of formula XIII may be prepared from an acid of formula IV, or a reactive derivative thereof, by reaction with the corresponding amine.

It is noted that many of the starting materials for synthetic methods as described above are commercially available and/or widely reported in the scientific literature.

In cases where compounds of formula I are sufficiently basic or acidic to form stable acid or basic salts, administration of the compound as a salt may be appropriate, and pharmaceutically acceptable salts may be made by conventional methods such as those described following. Examples of suitable pharmaceutically acceptable salts are organic acid addition salts formed with acids which form a physiologically acceptable anion, for example, tosylate, methanesulfonate, acetate, tartrate, citrate, succinate, benzoate, ascorbate, α-ketoglutarate, and α-glycerophosphate. Suitable inorganic salts may also be formed such as sulfate, nitrate, and hydrochloride.

Pharmaceutically acceptable salts may be obtained using standard procedures well known in the art, for example by reacting a sufficiently basic compound of formula I (or its ester) with a suitable acid affording a physiologically acceptable anion. It is also possible with most compounds of the invention to make a corresponding alkali metal (e.g., sodium, potassium, or lithium) or alkaline earth metal (e.g., calcium) salt by treating an amide of formula I (and in some cases the ester) with one equivalent of an alkali metal or alkaline earth metal hydroxide or alkoxide (e.g. the ethoxide or methoxide in aqueous medium followed by conventional purification techniques.

In vivo hydrolyzable esters of compounds of the invention may be made by coupling with a pharmaceutically acceptable carboxylic acid or an activated derivative thereof. For example, the coupling may be carried out by treating a parent amide of formula I with an appropriate acid chloride (for example, acetyl chloride, propionyl chloride, or benzoyl chloride) or acid anhydride (for example, acetic anhydride, propionic anhydride, or benzoic anhydride) in the presence of a suitable base such as triethylamine. Those skilled in the art will appreciate that other suitable carboxylic acids (including their activated derivatives) for the formation of in vivo hydrolyzable esters are known to the art and these are also intended to be included within the scope of the invention. Catalysts such as 4-dimethylaminopyridine may also be usefully employed.

When used to treat urinary incontinence, a compound of formula I is generally administered as an appropriate pharmaceutical composition which comprises a compound of formula I as defined hereinbefore together with a pharmaceutically acceptable diluent or carrier, the composition being adapted for the particular route of administration chosen. Such compositions are provided as a further feature of the invention.

The compositions may be obtained employing conventional procedures and excipients and binders and may be in a variety of dosage forms. For example, they may be in the form of tablets, capsules, solutions or suspensions for oral administration; in the form of suppositories for rectal administration; in the form of sterile solutions or suspensions for administration by intravenous, intravesicular, subcutaneous or intramuscular injection or infusion; or in the form of a patch for transdermal administration.

Treatment using a compound according to the invention may be remedial or therapeutic as by administering a compound following the onset or development of urinary incontinence in a patient. Treatment may also be prophylactic or prospective by administering a compound in anticipation that urinary incontinence may develop, for example in a patient who has suffered from incontinence in the past.

According to a further aspect, the invention provides the use of a compound of formula I, as defined hereinabove, in the manufacture of a medicament for the treatment of urinary incontinence.

It has also unexpectedly been found that compounds according to the invention are potassium channel openers. It is known that by functioning to open potassium channels, potassium channel opening compounds may thereby function to relax smooth muscle.

Because compounds according to the invention function to open cell potassium channels, they may also be useful as therapeutic agents in the treatment of other conditions or diseases in which the action of a therapeutic agent which opens potassium channels is desired or is known to provide amelioration. Such conditions or diseases include hypertension, asthma, peripheral vascular disease, right heart failure, congestive heart failure, angina, ischemic heart disease, cerebrovascular disease, renal cholic, disorders associated with kidney stones, irritable bowel syndrome, male pattern baldness, premature labor, and peptic ulcers.

The dose of compound of formula I which is administered will necessarily be varied according to principles well known in the art taking account of the route of administration, the severity of the incontinence condition, and the size and age of the patient. In general, a compound of formula I will be administered to a warm blooded animal (such as man) so that an effective dose is received, generally a daily dose of above 0.005, for example in the range of abut 0.01 to abut 10 mg/kg body weight.

It will be apparent to those skilled in the art that a compound of formula I may be co-administered with other therapeutic or prophylactic agents and/or medicaments that are not medically incompatible therewith. Compounds within the scope of the invention have not been found show any indication of untoward side-effects in laboratory test animals at several multiples of the minimum effective dose.

The actions of compounds of formula I as smooth muscle relaxants useful as therapeutic agents for the treatment of urinary incontinence through their action to open potassium channels and hyperpolarize the membrane electrical potential in bladder detrusor smooth muscle may be shown using suitably designed in vitro tests, such as the one described following.

Male albino Hartley guinea pigs (450–500 g) are sacrificed by carbon dioxide induced asphyxiation and quickly exsanguinated. The lower abdominal cavity is opened and the urinary bladder isolated. The bladder is cleaned of surrounding connective and adipose tissue, and the portion above the ureteral orifices is removed and washed in Krebs-Henseleit buffer solution of the following composition (in mM): NaCl 118.0, KCl 4.7, $MgSO_4$ 1.2, $KH_2PO_4$ 1.2, $CaCl_2$ 2.5, $NaHCO_3$ 25.0 and d-glucose 11.1. The solution is warmed to 37° C. and gassed with 95% $O_2$ and 5% $CO_2$. With vigorous bubbling, the solution should have a pH value close to 7.4.

The dome of the washed bladder is cut off and discarded; the remaining bladder is placed on a gauze in a Petri dish containing the buffer solution. A mid-ventral longitudinal cut is made with scissors to open the bladder. The strips cut from the dome and the base edge are discarded. The remaining detrusor mid-section is cut into two horizontal strips with an approximate width of 2.0 mm. These two strips are further bisected at the mid-dorsal section, creating four strip of similar dimensions. Each strip thus contains both dorsal and ventral portions of the bladder.

The two ends of each individual strip are tied to a glass support rod and a force-displacement transducer (Grass model FT03), respectively, with 4-0 black braided silk suture.

The transducers are connected to a polygraph (Grass model 7E), which is calibrated at 5 mV/cm and the calibration checked for linearity with weights of 5 and 0.5 grams. The analog electrical output signals from the polygraph are digitized by a Modular Instrument Micro 5000 signal processing system using Biowindow Data Acquisition Software, which is run under the Microsoft OS/2 operating system with an IBM-compatible PC.

The detrusor strips on the glass rod are secured in 20 ml tissue baths and allowed to equilibrate under a preload tension of 2 grams. During the following 45 to 60 min equilibration period, the tissue is washed with fresh buffer solution at 15 min interval, with the tension adjusted, if necessary, to 2 grams prior to washing. After the equilibration period, a priming dose of 15 mM KCl (total concentration in the bath) is applied. The tissue is washed after 10 min and washed twice more at 15 min intervals with tension adjusted to 2 grams before each washing.

When the tissue relaxes to a steady state after the final washing, 15 mM KCl is again applied. Once the myogenic activity of the tissue reaches a steady state, the baseline data are acquired through the Biowindows Data Acquisition System by averaging 5 min of the myogenic data sampled at 32 Hz. Once the baseline is acquired, the experimental compounds are dosed in a cumulative manner in half log unit increments. The contact time for each dose is 10 min with the final 5 min being the period of time that the dose response data are acquired. If 30 µM of the test compound does not abolished the detrusor mechanical activity, then 30 µM cromakalim, a putative potassium channel opener, is dosed to establish a maximum response. The effect of the compound at each dose is expressed as % of the maximum inhibitory response, which is further normalized with respect to the corresponding effect of the compound vehicle control. The normalized response is then used to derive the $IC_{50}$ of the relaxant activity of the compound through the application of Marquardt's nonlinear iterative curve fitting technique to a standard dose-response function.

In general, compounds of the invention demonstrate significant acitivity in the above described test at a concentration of 30 micromolar. Preferred compounds typically exhibit an $IC_{50}$ on the order of 30 micromolar or less in the test. For example, the compound of Example 5 has been found to give an $IC_{50}$ of 6.44. $IC_{50}$ is a well understood term and means the concentration of test compound which causes a 50% decrease in the in vitro contraction of the bladder tissue described in the above test.

The ability of compounds according to the invention to open potassium channels in detrusor smooth muscle can be further demonstrated by a second in vitro test.

This second in vitro test is similar to the one described above with regard to tissue preparation and data acquisition. However, the following exceptions are noted. In this second test, the contraction of the detrusor strips during priming and after the equilibration period is achieved with 80 mM instead of 15 mM KCl (total concentration in the bath). A sustained tension in the tissue is evident after this high KCl stimulation, because voltage-sensitive calcium channels have been rendered open to permit an influx of calcium into the cells and the development of tonic tension. This tension is totally abolished with 300 µM of papaverine, which is thereby used to establish the maximum response in this test.

Typical calcium channel blockers like nifedipine, nimodipine, isradipine, and verapamil are able to relax and reduce the myogenic activity of guinea pig detrusor strips in both tests by virtue of their blocking action on calcium channels. However, all of the aforementioned calcium channel blockers are more potent in the second test when 80 mM KCl is used, than in the first test where 15 mM KCl is used. In contrast, while the putative potassium channel opener cromakalim has a potent relaxant activity in the first test with an $IC_{50}$ in the range of 0.6 to 0.9 µM, it demonstrates insignificant relaxant activity in the second test at concentrations as high as 30 µM. Thus, the profile of a higher relaxant activity in the first test than in the second of compounds according to the invention indicates that the compounds are functioning as potassium channel openers.

The ability of the compounds according to the invention to act as potassium channel openers on bladder tissue may be further demonstrated by a standard test which measures the effect of test compounds on the rate of efflux of rubidium from the tissue.

The following is a description of a test in vivo which is complimentary to the above described test and which may be used to ascertain if a test compound is active and, additionally, if the test compound exhibits selectivity for the bladder without significant cardiovascular effects when dosed orally.

Male Wistar rats (400–500 g) were anesthetized with 50 mg/kg Nembutal, i.p. For each rat, the abdominal region and the front and back of the neck were shaved and povidone-iodine was applied to the skin. For carotid catheterization, the left carotid artery was exposed via a small ventral cervical incision. The exposed area was flushed with a 2% lidocaine HCl solution to relax the vessel. The catheter, filled with 0.9% saline, was introduced approximately 2.4 cm into the artery so that its tip resided in the aortic arch. The distal end of the catheter was exteriorized at the nape of the neck, filled with heparin (1000 units/ml) and heat sealed. For bladder catheterization, the bladder was exposed through a midline abdominal incision. A trocar was passed through the abdominal muscle about 1 cm from the upper end of the incision and then tunneled subcutaneously to emerge through the skin at the back of the neck. A saline-filled catheter was passed through the trocar. A small opening in the bladder dome was created with an Accu-Temp cautery. The catheter was placed into the bladder and secured with a 4-0 silk ligature. The catheter was flushed with saline and patency was noted. The external end of the catheter was heat-sealed to prevent urine leakage. The abdominal muscles and the skin were sutured. Both catheters were threaded through a stainless steel anchor button (Instech), which was then sutured to the subcutaneous muscle at the point of exteriorization. The skin was sutured closed over the button. The animals were allowed to recover from anesthesia.

24–48 hours after surgery, each rat was placed in a metabolism cage and connected via the anchor button to an Instech spring tether and swivel system to protect the catheters from damage and to allow the animal free movement in the cage. The carotid catheter was connected to a Gould P23XL pressure transducer for blood pressure measurement. The bladder catheter was connected to a pump for saline infusion and to a pressure transducer by means of PE50 tubing and a 4-way stopcock. A toploading balance with a collection cup was placed under the cage for urine output measurement.

The rats were weighed, orally sham-dosed (dosing needle introduced, but no fluid expelled), and transvesical saline infusion (0.18 ml/min) was begun and continued throughout the experiment. Variations in blood pressure, heart rate, intravesical pressure and urine output were recorded on either a Grass Polygraph or a Gould TA4000 recording system. The animals were allowed to equilibrate until the micturition pattern became consistent (approx. 45–90 min.). At this point, a basal level of each experimental parameter was recorded and the rats were administered by oral gavage the appropriate dose of compound (in a 75% PEG 400 - saline vehicle) in concentrations such that the volume was 1 ml/kg body weight. The effects of the compounds on experimental parameters were followed for five hours after administration.

Experimental results for both the interval between contractions and also heart rates were expressed as the mean ±S.E.M. (Standard Error of Measures) % change from basal level, with each animal serving as its own control. MAP is expressed as mean ±S.E.M mm Hg change from basal level.

Compounds according to the invention typically demonstrate significant activity in one or more of the above-described tests.

The invention will now be illustrated by the following non-limiting examples in which, unless stated otherwise:

(i) temperatures are given in degrees Celsius (°C); operations were carried out at room or ambient temperature, that is, at a temperature in the range of 18°–25° C.;

(ii) organic solutions were dried over anhydrous magnesium sulfate; evaporation of solvent was carried out using a rotary evaporator under reduced pressure (600–4000 pascals; 4.5–30 mm Hg) with a bath temperature of up to 60° C.;

(iii) chromatography means flash chromatography on silica gel; thin layer chromatography (TLC) was carried out on silica gel plates;

(iv) in general, the course of reactions was followed by TLC and reaction times are given for illustration only;

(v) melting points are uncorrected and (dec) indicates decomposition; the melting points given are those obtained for the materials prepared as described; polymorphism may result in isolation of materials with different melting points in some preparations;

(vi) final products had satisfactory proton nuclear magnetic resonance (NMR) spectra;

(vii) yields are given for illustration only and are not necessarily those which can be obtained by diligent process development; preparations were repeated if more material was required;

(viii) when given, NMR data is in the form of delta values for major diagnostic protons, given in parts per million (ppm) relative to tetramethylsilane (TMS) as an internal standard, determined at 300 MHz using perdeuterio dimethyl sulfoxide (DMSO-$d_6$) as solvent; coupling constants (J) are given in Hz; Ar designates an aromatic proton when such an assignment is made;

(ix) chemical symbols have their usual meanings; SI units and symbols are used;

(x) reduced pressures are given as absolute pressures in pascals (Pa); elevated pressures are given as gauge pressures in bars;

(xi) solvent ratios are given in volume:volume (v/v) terms; and (xii) mass spectra (MS) were run with an electron energy of 70 electron volts in the chemical ionization (CI) mode using a direct exposure probe; where indicated ionization was effected by electron impact (EI) or fast atom bombardment (FAB); values for m/z are given; generally, only ions which indicate the parent mass are reported.

EXAMPLE 1.

3,3,3-Trifluoro-2-hydroxy-2-methyl-N-[4-(1-piperidinylsulfonyl)phenyl]propanamide.

A solution of 3,3,3-trifluoro-N-[4-(fluorosulfonyl)phenyl]-2-hydroxy-2-methylpropanamide (0.2 g), piperidine (0.1 g), and 4-dimethylaminopyridine (5 mg) in dry acetonitrile (4 ml) was heated at reflux for 3 hours. After cooling to 22° C., the reaction mixture was diluted with water (30 ml) and extracted with ethyl acetate (3×15 ml). The combined organic extracts were washed with 1N HCl, brine, dried ($Na_2SO_4$), and the solvent evaporated under reduced pressure. Recrystallization from methyl-t-butyl ether/hexane gave the title compound as a colourless crystalline solid, (0.2 g); mp 164°–166° C.; MS: m/z=381(M+1); NMR (250 MHz, $CDCl_3$): 1.42 (m, 2), 1.64 (m, 4), 1.77 (s,3), 2.97 (t,4), 3.79 (s,1), 7.73 (s), 8.67 (s,1). Analysis for $C_{15}H_{19}F_3N_2O_4S$: Calculated: C, 47.36; H, 5.03; N, 7.37. Found: C, 47.38; H, 5.16; N, 7.30.

The starting 3,3,3-trifluoro-N-[4-(fluorosulfonyl)phenyl]-2-hydroxy-2-methylpropanamide was prepared as follows.

To a cooled (−20° C.) solution of α-trifluoromethyl lactic acid (2.0 g) in dry N,N-dimethylacetamide (15 ml) was added thionyl chloride (0.97 mL) dropwise over 10 minutes. The reaction mixture was stirred at −20° C. for 1 hour, warmed to 0° C. over 1 hour, then treated with sulfanilyl fluoride (2.22 g) in one portion and heated at 100° C. for 24 hours. After cooling to 22° C. the reaction mixture was diluted with water (150 ml) and extracted with ethyl acetate (3×35 ml). The combined organic extracts were washed with water, brine, dried and the solvent removed under reduced pressure. The crude product was purified by chromatography (13:1 $CH_2Cl_2$:$Et_2O$) and recrystallised from methyl-t- butyl ether to give 3,3,3-trifluoro-N-[4-(fluorosulfonyl) phenyl]-2-hydroxy-2-methylpropanamide as colourless crystals, (1.7 g); mp 152°–154° C.; MS: m/z=316(M+1); NMR (CDCl₃): 1.78 (s,3), 3.51 (broad s), 7.86–7.89 (m, 2), 7.99–8.03 (m,2), 8.79 (broad s,1). Analysis for $C_{10}H_9F_4NO_4S$: Calculated: C, 38.10; H,2.88; N, 4.44; Found: C, 38.21; H, 2.97; N, 4.44.

EXAMPLE 2.

3,3,3-Trifluoro-2-hydroxy-2-methyl-N-[4-(1-pyrrolidinylsulfonyl)phenyl]propanamide.

A solution of 3,3,3-trifluoro-N-(4-flurosulfonylphenyl)-2-hydroxy-2-methylpropanamide (0.25 g), pyrrolidine (0.28 g), and 4-pyrrolidinopyridine (12 mg) in dry acetonitrile (3 ml) was heated at reflux for 24 hours. After cooling to 22° C., the reaction mixture was diluted with water (25 ml) and extracted with ethyl acetate (3×15 ml). The combined organic extracts were washed with 1N HCl, brine, dried (Na₂SO₄) and evaporated to give an oil which crystallized upon suspension in hexane to yield the title compound as an off-white crystalline solid (0.27 g); mp 183°–186° C.; MS: m/z=367(M+1); NMR: 1.59 (s,3), 1.62 (m,4), 3.12 (m,4), 7.56 (s,1), 7.75–7.77 (m,2), 8.00–8.03 (m,2), 10.40 (s,1). Analysis for $C_{14}H_{17}F_3N_2O_4S$: Calculated: C, 45.89; H, 4.68; N, 7.65; Found: C, 45.98; H, 4.76; N, 7.56.

EXAMPLE 3.

3,3,3-Trifluoro-2-hydroxy-2-methyl-N-[4-(morpholinosulfonyl)phenyl]propanamide.

Following the method of Example 1, but using morpholine instead of piperidine and purifying the crude reaction product by chromatography (6:1 CH₂Cl₂: ethyl acetate), the title compound was obtained as a colourless solid (76.8 mg); mp 165°–167° C.; MS: m/z=383(M+1); NMR (250 MHz): 1.59 (s,3), 2.81–2.85 (m,4), 3.60–3.63 (m,4), 7.58 (s,1), 7.66–7.71 (m,2), 8.04–8.08 (m,2), 10.45 (s,1). Analysis for $C_{14}H_{17}F_3N_2O_5S$: Calculated: C, 43.97; H, 4.48; N, 7.33; Found: C, 44.10; H, 4.54; N, 7.18.

EXAMPLE 4.

3,3,3-Trifluoro-2-hydroxy-2-methyl-N-[4-(thiomorpholinosulfonyl)phenyl]propanamide.

Following the method of Example 1, but using thiomorpholine instead of piperidine, and recrystallising the crude reaction product from methyl-t-butyl ether/hexane, the title compound was obtained as a colourless solid (0.24 g); mp 182°–185° C.; MS: m/z=399(M+1); NMR (250 MHZ): 1.60 (s,3), 2.64–2.68 (m,4), 3.16–3.20 (m,4), 7.58 (s,1), 7.69–7.72 (m, 2), 8.03–8.07 (m,2), 10.43 (s,1). Analysis for $C_{14}H_{17}F_3N_2O_4S_2$ calculated: C, 42.20; H, 4.30; N, 7.03; Found: C, 42.57; H, 4.50; N, 6.99.

EXAMPLE 5

N-[4-(N,N-Dipropylaminosulfonyl)phenyl]-3,3,3-trifluro-2-hydroxy-2-methylpropanamide.

A solution of 3,3,3-trifluoro-N-[4-(fluorosulfonyl)phenyl] -2-hydroxy-2-methylpropanamide (0.2 g), di-n-propylamine (0.25 g), and 4-dimethylaminopyridine (13.0 mg) in dry acetonitrile (3 ml) was heated at reflux for 4 days. The reaction mixture was cooled to 22° C., diluted with water (30 ml) and extracted with ethyl acetate (2×15 ml). The combined ethyl acetate extracts were washed with 1N HCl, brine, dried and evaporated to give an oil. The oil was purified by chromatography (12:1 CHCl₃: diethyl ether) to yield an oil which crystallized from hexane to produce the title compound as a colourless crystalline solid (87.5 mg); mp 132°–134° C.; MS: m/z=397(M+1); NMR (250M Hz): 0.77–0.83 (t,6), 1.41–1.49 (m,4), 1.58 (s,3), 2.96–3.02 (t,4), 7.54 (s,1), 7.72–7.75 (m,2), 7.96–7.98 (m,2), 10.36 (s,1). Analysis for $C_{16}H_{23}F_3N_2O_4S$: Calculated: C, 48.47; H, 5.85; N, 7.07; Found: C, 48.84; H, 5.90; N, 6.89.

EXAMPLE 6.

N-[4-(N,N-Dimethylaminosulfonyl)phenyl]-3,3,3-trifluoro-2-hydroxy-2-methylpropanamide.

To a cooled (-10° C.) solution of α-trifluoromethyl lactic acid (0.69 g) in dry N,N-dimethylacetamide (5 ml) was added thionyl chloride (0.33 ml) dropwise over 2 minutes. The mixture was stirred at −10° C. for 90 minutes, then treated successively with 4-pyrrolidinopyridine (13 mg), di-isopropylethylamine (0.76 ml), and 4-(N,N-dimethylaminosulfonyl)aniline (0.88 g). The reaction mixture was stirred at 22° C. for 48 hours, then diluted with water and extracted with ethyl acetate. The combined ethyl acetate extracts were washed with 1N HCl, brine, dried and the solvent evaporated. The crude product was purified by chromatography (12:1 CH₂Cl₂: ethyl acetate) and recrystallised from methyl-t-butyl ether/hexane to give the title compound as a colourless crystalline solid (0.56 g); mp 139°–141° C.; MS: m/z=341(M+1); NMR (250 MHz): 1.60 (s,3), 2.58 (s,6), 7.58 (s,1), 7.69–7.73 (d,2), 8.03–8.06 (d,2). Analysis for $C_{12}H_{15}F_3N_2O_4S$: Calculated: C, 42.35; H, 4.44; N, 8.23; Found: C, 42.21; H, 4.54; N, 8.15.

The starting 4-(N,N-dimethylaminosulfonyl)aniline was prepared as follows.

To a suspension of p-acetamidobenzenesulfonyl chloride (2.0 g) in dry acetonitrile (15 ml) at 22° C. was added 40% aqueous dimethylamine (30 ml), and the mixture was stirred for 18 hours. The reaction mixture was concentrated and partitioned between ethyl acetate and water. The ethyl acetate was washed with brine, dried (Na₂SO₄), and evaporated under reduced pressure to give a colourless crystalline solid (1.17 g). This was dissolved in ethanol and the resultant solution was treated with concentrated hydrochloric acid and heated to reflux. The reaction mixture was then cooled to 22° C. and adjusted to pH 8 with concentrated NH₄OH. The resultant suspension was cooled, filtered, the solvent washed with water and dried to give a light tan solid (0.88 g); MS: m/z=201(M+1); NMR: 2.50 (s,6), 6.04 (broad s,2), 6.65 (d,2), 7.35 (d,2).

EXAMPLE 7.

N-[4-(Aminosulfonyl)phenyl]-3,3,3-trifluoro-2-hydroxy-2-methylpropanamide.

To a cooled (−20° C.) solution of α-trifluoromethylacetic acid (0.2 g) in dry N,N-dimethylacetamide (4 ml) was added thionyl chloride (0.16 g) in one portion. The mixture was stirred for 15 minutes, warmed to −5° C. over 45 minutes, then treated with sulfanilamide (0.21 g). The mixture was warmed to 22° C. and stirred for 6 hours, then diluted with water (40 ml) and extracted with ethyl acetate (4×15 ml). The organic extracts were combined and washed with brine, dried, and concentrated in vacuo to give an oil. Purification by chromatography (2:1 ethyl acetate: hexane) and recrystallisation from methyl-t-butyl ether/hexane gave the title compound as a pale yellow crystalline solid (0.17 g); mp 179°–182° C.; MS: m/z=313(M+1); NMR (250 MHz): 1.58 (s,3), 7.29 (s,2), 7.54 (s,1), 7.74–7.77 (m,2), 7.89–7.93 (m,2), 10.28 (s,1). Analysis for $C_{10}H_{11}F_3N_2O_4S$: Calculated: C, 38.46; H, 3.55; N, 8.97; Found: C, 38.34; H, 3.51; N, 8.89.

EXAMPLE 8.

N-[4-(N,N-Diethylaminosulfonyl)phenyl]-3,3,3-trifluoro-2-hydroxy-2-methylpropanamide.

To a solution of α-trifluoromethyl lactic acid (0.37 g) in dry tetrahydrofuran (10 ml) at 22° C. was added carbonyldiimidazole (0.38 g) in one portion. The mixture was stirred for 30 minutes, then treated with 4-(N,N-diethylaminosulfonyl)aniline (0.53 g) and stirred at 22° C. for 1 hour followed by heating at reflux for 18 hours. After cooling to 22° C., the mixture was concentrated to an oil which was purified by chromatography (9:1 $CH_2Cl_2$: diethyl ether) and crystallization from hexane to produce the title compound as a colourless crystalline solid (0.15 g); mp 115°–130° C.; MS: m/z=341(M+1); NMR (250 MHz, $CDCl_3$): 1.12 (t,6), 1.78 (s,3), 3.22 (s,4), 3.73 (s,1), 7.67–7.79 (m,4), 8.62(broad s,1). Analysis for $C_{14}H_{19}F_3N_2O_4S$: Calculated: C, 45.64; H, 5.19; N, 7.61; Found: C, 45.74; H, 5.22; N, 7.66.

The starting 4-(N,N-diethylaminosulfonyl)aniline was prepared as follows.

A mixture of sulfanilic acid (2.0 g) and phosphorous pentachloride (5.97 g) was heated to 140° C., the resulting melt stirred for 10 minutes, then treated cautiously with phosphorous oxychloride (50 ml) and heated at reflux for 3 hours. After cooling to 22° C., the reaction mixture was carefully poured onto ice (600 g) and vigorously stirred for 30 minutes. The suspension was filtered and the solid washed with water and dried to give 2.3 g of hydroscopic intermediate N-(4-chlorosulfonylphenyl)phosphoramidyl dichloride. A solution of the phosphoramidyl dichloride (1.2 g) in diethyl ether (35 ml) was treated with diethylamine (5.17 ml) and the resulting suspension heated at reflux for 48 hours. After evaporation of diethyl ether at reduced pressure, the pale white solid was treated with concentrated hydrochloric acid (60 ml) and heated at reflux for 8 hours. Upon cooling to 0° C. and adjustment to pH 8 with concentrated ammonium hydroxide, the solid suspension was filtered, washed with water and dried to give of 4-(N,N-diethylaminosulfonyl)aniline as a colourless crystalline solid (0.54 g); MS: m/z=229(M+1); NMR ($CDCl_3$): 1.11 (t,6), 3.19 (q,4), 4.08 (broad s,2), 6.65–6.68 (m,2), 7.56–7.59 (m,2).

EXAMPLE 9.

3,3,3-Trifluoro-2-hydroxy-2-methyl-N-[4-(N-phenyl-N-methylaminosulfonyl)phenyl] propanamide.

To a cooled (−20° C.) solution of α-trifluoromethyl lactic acid 0.20 g in dry N,N-dimethylacetamide (4 ml) was added thionyl chloride (0.16 g). The reaction mixture was stirred for 1 hour, then warmed to 0° C. over 30 minutes and treated with 4-(N-phenyl-N-methylaminosulfonyl)aniline (0.34 g). After stirring at 22° C. for 24 hours, the reaction mixture was diluted with water (30 ml) and extracted with ethyl acetate (2×20 ml). The combined ethyl acetate extracts were washed with brine, dried ($Na_2SO_4$) and concentrated at reduced pressure to give an oil which was purified by chromatography (1:1 hexane: ethyl aceate) and recrystallised from methyl-t-butyl ether/hexane to produce the title compound as a colourless solid (0.31 g); mp 147°–149° C.; MS: m/z=403(M+1); NMR (250 MHz): 1.55 (s,3), 3.09 (s,3), 7.05–7.08 (m, 2), 7.28–7.43 (m,5), 7.53 (s,1), 7.91–7.95 (m,2), 10.36 (broad s, 1). Analysis for $C_{17}H_{17}F_3N_2O_4S$: Calculated: C, 50.78; H, 4.26; N, 6.97; Found: C, 50.80; H, 4.37; N, 6.93.

The starting 4-(N-phenyl-N-methylaminosulfonyl)aniline was prepared as follows.

A suspension of N-(4-chlorosulfonylphenyl) phosphoramidic dichloride (1.0 g) and N-methylaniline (2.49 g) in water (5 ml) was heated at reflux for 18 hours. After cooling to 0° C. and adjustment to pH2 with concentrated hydrochloric acid, the suspension was heated at reflux for 30 minutes, then cooled to 0° C. and adjusted to pH 8 with concentrated ammonium hydroxide. The suspension was extracted with ethyl acetate (3×40 ml), the combined organic extracts were washed with brine, dried ($Na_2SO_4$), and concentrated to an oil. Purification by chromatography (3:2 hexane: ethyl acetate) gave 4-(N-phenyl-N-methylaminosulfonyl)aniline as a colourless crystalline solid (0.65 g); MS: m/z=263(M+1); NMR ($CDCl_3$): 3.13 (s,3), 4.11 (broad s,2), 6.58–6.62 (m, 2), 7.10–7.13 (m,2), 7.23–7.31 (m,s).

EXAMPLE 10.

4,4,4-Trifluoro-3-hydroxy-3-methyl-1-[4-(1-pyrrolidinylsulfonyl)phenyl]but-1-yne.

To a solution of the 4-(1-pyrrolidinylsulfonyl) phenylacetylene (1.3 g) in anhydrous tetrahydrofuran (60 mL) cooled to −78° C. under a nitrogen atmosphere was added n-butyllithium (2.43 mL of a 2.5M solution in hexanes, 6.09 mmol). The anion was generated over a ten minute period at −78° C. To the anion was added a cooled (0° C.) solution of trifluoroacetone (644 mL) in anhydrous tetrahydrrofuran (10 mL) over a 20 second period. The reaction was stirred at −78° C. for five minutes before the ice bath was removed. After an additional five minutes, the reaction was quenched with 2N HCl (50 mL). The product was extracted into diethyl ether. The combined organic extracts were dried, filtered, and evaporated under reduced pressure. The crude product was purified by chromatography (1:3 acetone: hexanes) followed by recrystallization (1:1 diethyl ether:hexanes) to yield the title compound as a white solid (1.38 g); mp 167.8°–168.7° C.; MS: m/z=348(M+1); NMR (CDCl3): 1.74 (s,3), 1.71–1.78 (m,4), 3.15 (s,1), 3.21–3.26.(m,4), 7.56–7.59 (m,2), 7.77–7.80 (m,2). Analysis for $C_{15}H_{16}F_3NO_3S$: Calculated: C, 51.87; H, 4.64; N, 4.03; Found: C, 51.80; H, 4.67; N, 3.88.

a. 4-(1-Pyrrolidinylsulfonyl)iodobenzene. To a solution of 4-iodobenzenesulfonyl chloride (10 g), in anhydrous tetrahydrofuran (140 mL) under a nitrogen atmosphere at ambient temperature was added 4-methylmorpholine (3.6 mL), 4-pyrrolidinopyridine (300 mg), and pyrrolidine (2.3 mL). The reaction mixture was stirred at room temperature for 1.5 hours at which time the volatile materials were removed under reduced pressure. The crude reaction mixture was partitioned between ethyl acetate and water. The aqueous phase was further extracted with ethyl acetate and the combined organic layers washed with 2N hydrochloric acid and brine respectively, prior to drying. The material was evaporated and purified by crystallization with 1:9 diethyl ether:hexanes. The resulting solid was isolated and dried under reduced pressure to provide the sulfonamide as a white solid (8.8 g); mp 129°–133° C.; MS: m/z=338(M+1);

NMR (CDCl3): 1.73–1.80 (m,4), 3.21–3.26 (m,4), 7.53–7.57 (m,2), 7.86–7.92 (m,2).

b. 4-(1-Pyrrolidinylsulfonyl)phenylacetylene. To a solution of the 4-(1-pyrrolidinylsulfonyl)iodobenzene (5.0 g) in diethyl amine (130 mL) under a nitrogen atmosphere at ambient temperature was added trimethylsilyl acetylene (2.9 mL), bis(triphenylphosphine) palladium(II)chloride (523 mg), and copper(I)iodide (57 mg). After 1.5 hours the diethyl amine was removed under reduced pressure. To crude reaction mixture was then added methanol (75 mL) followed by 2N sodium hydroxide (20 mL). After 15 minutes the reaction was neutralized with 2N hydrochloric acid and the methanol was evaporated. The aqueous phase was extracted with ethyl acetate. The combined organic phases were dried, filtered, and evaporated. The crude product was purified by chromatography (1:3 acetone:hexanes) to yield the acetylene as an off-white solid (2.40 g); mp 140°–143° C.; MS: m/z=236 (M+1); NMR (CDCl3): 1.72–1.81 (m,4), 3.22–3.27 (m,5), 7.61–7.64 (m, 2), 7.77–7.81 (m,2).

EXAMPLE 11.

4,4,4-Trifluoro-3-hydroxy-3-methyl-1-[4-(1-pyrrolidinylsulfonyl)phenyl]-trans-but-1-ene.

To a solution of sodium bis(methoxyethoxy) aluminum hydride (720 mL of a 3.4M solution in toluene, 2.45 mmol) in anhydrous diethyl ether (6 mL) cooled to –2° C. under a nitrogen atmosphere was added dropwise an ethereal solution (25 mL) of 4,4,4-trifluoro-3-hydroxy-3-methyl-1-[4-(1-pyrrolidinylsulfonyl)phenyl]but-1-yne (500 mg). The rate of addition was adjusted such that the reaction temperature (internal) did not exceed 10° C. Upon complete addiron the reaction was kept near 0° C. After 30 minutes the reaction was quenched by the addition of 3M sulfuric acid (20 mL). The product was extracted into diethyl ether. The combined organic extracts were dried, filtered, and evaporated. The crude product was adsorbed onto silica gel and purified by chromatography (1:8 diethyl ether: chloroform) to yield a white compound (447 mg). This material was further purified by recrystalization employing diethyl ether:hexanes (1:5) to provide the title compound (251 mg); mp 119°–121° C.; MS: m/z=350(M+1); NMR: (CDCl3): 1.59 (s,3), 1.73–1.78 (m,4), 2.45 (s,1), 3.22–3.27 (m,4), 6.41 (d,1, J=16.0), 6.93 (d,1,J=16.0), 7.52–7.55 (m,2), 7.77–7.81 (m,2). Analysis for $C_{15}H_{18}F_3NO_3S$: Calculated: C, 51.57; H, 5.19; N, 4.01; Found: C, 51.45; H, 5.19; N, 3.90.

EXAMPLE 12.

4,4,4-Trifluoro-3-hydroxy-3-methyl-1-[4-(N-methyl-N-phenylaminosulfonyl)phenyl]but-1-yne.

Using a procedure similar to that described in Example 10.c., but employing 4-(N-methyl-N-phenylaminosulfonyl) phenyl acetylene instead of 4-(1-pyrrolidinylsulfonyl) phenylacetylene and purifying the crude product by chromatography (3:1 hexaes:ethyl acetate) followed by trituration with hexanes, the title compound was prepared as a white solid; mp 116.5°–118.4° C.; MS: m/z=384(M+1); NMR (CDCl3): 1.74 (s,3), 2.85 (s,1), 3.18 (s,3), 7.06–7.09 (m,2), 7.26–7.34 (m, 3), 7.47–7.53 (m, 4). Analysis for $C_{18}H_{16}F_3NO_3S$: Calculated: C, 56.39; H, 4.21; N, 3.65; Found: C, 56.50; H, 4.17; N, 3.65.

a. 4-(N-Methyl-N-phenylaminosulfonyl)iodobenzene. Using a procedure similar to that described in Example 10.a., but employing N-methylaniline instead of pyrrolidine and purifying the crude product by recrystalization (1:4 metyl-t-butyl ether:hexane), the sulfonamide was prepared; MS: m/z=374(M+1); NMR (CDCl3): 3.18 (s,3), 7.08–7.11 (m,2), 7.22–7.34 (m,5), 7.78–7.83 (m,2).

b. 4-(N-Methyl-N-phenylaminosulfonyl) phenylacetylene. Using a procedure similar to that described in Example 10.b., but employing 4-(N-methyl-N-phenylaminosulfonyl)iodobenzene instead of 4-(1-pyrrolidinylsulfonyl)iodobenzene and purifying the crude product by chromatography (methylene chloride) the acetylene was prepared; MS: m/z=272(M+1); NMR (CDCl3): 3.18 (s,3), 3.42 (s,1), 7.06–7.10 (m,2), 7.25–7.34 (m,3), 7.47–7.61 (m,4).

EXAMPLE 13.

4,4,4-Trifluoro-3-hydroxy-3-methyl-1-[4-(N-Methyl-N-phenylaminosulfonyl)phenyl]-trans-but-1-ene.

Following the method of Example 11, but employing 4,4,4-trifluoro-3-hydroxy-3-methyl-1-[4-(N-methyl-N-phenylaminosulfonyl)phenyl]but-1-yne instead of 4,4,4-trifluoro-3-hydroxy-3-methyl-1-[4-(1-pyrrolidinylsulfonyl) phenyl]but-1-yne and purifying by trituration with hexanes, the title compound was prepared as a white solid; mp 146°–148° C.; MS: m/z=386(M+1); NMR (CDCl3): 1.58 (s,3), 3.15 (s,1), 3.17 (s,3), 6.40 (d,1, J=15.9), 6.90 (d,1, J=16.0), 7.07–7.10 (m,2), 7.26–7.33 (m,3), 7.42–7.50 (m,4). Analysis for $C_{18}H_{18}F_3NO_3S$: Calculated: C, 56.10; H, 4.71; N, 3.63. Found: C, 55.79; H, 4.70; N, 3.50.

EXAMPLE 14.

1-[4-(N,N-Diethylaminosulfonyl)phenyl]-4,4,4-trifluoro-3-hydroxy-3-methylbut-1-yne.

Using a procedure similar to that described in Example 10, but employing 4-(N,N-diethylaminosulfonyl) phenylacetylene instead of 4-(1-pyrrolidinylsulfonyl) phenylacetylene and purifying the crude product by chromatography (3:1 hexaes:ethyl acetate), the title compound was obtained as a white solid; mp 140.5°–144.3° C.; MS: m/z=350(M+1); NMR (CDCl3): 1.11 (t,6), 1.73 (s,3), 2.87 (s,1), 2.23 (dd,4), 7.53–7.56 (m,2), 7.75–7.78 (m,2). Analysis for $C_{15}H_{18}F_3NO_3S$: Calculated: C, 51.57; H, 5.19; N, 4.01; Found: C, 51.33; H, 5.07; N, 3.93.

a. 4-(N,N-Diethylaminosulfonyl)iodobenzene. Using a procedure similar to that described in Example 10.a., but employing diethylamine instead of pyrrolidine and purifying the crude product by trituration with hexanes, the title compound was obtained; MS: m/z=340(M+1); NMR (CDCl3): 1.13 (t,6), 3.23 (dd,4), 7.50–7.54 (m,2), 7.83–7.86 (m,2).

b. 4-(N,N-Diethylaminosulfonyl)phenylacetylene. Using a procedure similar to that described in Example 10.b., but employing 4-(N,N-diethylaminosulfonyl)iodobenzene instead of 4-(1-pyrrolidinylsulfonyl)iodobenzene and purifying the crude product by recrystalization (diethyl ether:hexane) the title compound (23%) was obtained; MS: m/z=238(M+1); NMR (CDCl3): 1.13 (t,6), 3.21–3.28 (m,5), 7.58–7.61 (m,2), 7.75–7.78 (m,2).

EXAMPLE 15.

1-[4-(N,N-Diethylaminosulfonyl)phenyl]-4,4,4-trifluoro-3-hydroxy-3-methyl-trans-but-1-ene.

Using a procedure similar to that described in Example 11, but substituting 1-[4-(N,N-diethylaminosulfonyl)

phenyl]-4,4,4-trifluoro-3-hydroxy-3-methylbut-1-yne for the 4,4,4-trifluoro-3-hydroxy-3-methyl-1-[4-(1-pyrrolidinylsulfonyl)phenyl]but-1-yne used therein, the title compound was prepared; mp 112.1°–117.2° C.; MS: m/z= 352(M+1). Analysis for $C_{15}H_{20}F_3NO_3S$: Calculated: C, 51.27; H, 5.74; N, 3.99. Found: C, 51.17; H, 5.96; N, 3.87.

EXAMPLE 16.

3,3,3-Trifluoro-2-hydroxy-2-methyl-N-[4-(N-phenylaminosulfonyl)phenyl]propanamide.

Using a sequence similar to that described in Example 6, but substituting aniline for the dimethylamine used in 6.a., the title compound was prepared; MS: m/z=389(M+1). Analysis for $C_{16}H_{15}F_3N_2O_4S$: Calculated: C, 49.48; H, 3.89; N, 7.21; Found: C, 49.51: H, 3.89; N, 7.18.

EXAMPLE 17.

N-[4-(N,N-Diphenylaminosulfonyl)phenyl]-3,3,3-trifluoro-2-hydroxy-2-methylpropanamide.

Using a sequence similar to that described in example 6, but substituting diphenylamine for the dimethylamine used in 6.a., the title compound was prepared; mp 217°–220° C.; MS: m/z=465(M+1). Analysis for $C_{22}H_{19}F_3N_2O_4S$: Calculated: C, 56.89; H, 4.12; N, 6.03. Found: C, 56.92; H, 4.25; N, 5.96.

EXAMPLE 18.

4,4,4-Trifluoro-3-hydroxy-3-methyl-1-[4-(morpholinosulfonyl)phenyl]-trans-but-1-ene.

4,4,4-Trifluoro-3-hydroxy-3-methyl-1-[4-(morpholinosulfonyl)phenyl]but-1-yne was subjected to conditions similar to those described in Example 11 to give the title compound; mp 141.9°–142.2° C.; MS: m/z=366 (M+1). Analysis for $C_{15}H_{18}F_3NO_4$: Calculated: C, 49.31; H, 4.97; N, 3.83. Found: C, 48.98; H, 5.03; N, 3.68.

The starting 4,4,4-trifluoro-3-hydroxy-3-methyl-1-[4-(morpholinosulfonyl)phenyl]but-1-yne was prepared using a sequence similar to that described in Example 10, except substituting morpholine for the pyrrolidine used therein.

EXAMPLE 19.

The following illustrate representative pharmaceutical dosage forms containing a compound of formula I, for example as illustrated in any of the previous Examples, (hereafter referred to as "compound X"), for therapeutic or prophylactic use in humans:

|  | mg/tablet |
|---|---|
| (a) Tablet |  |
| Compound X | 50.0 |
| Mannitol, USP | 223.75 |
| Croscarmellose sodium | 6.0 |
| Maize starch | 15.0 |
| Hydroxypropylmethylcellulose (HPMC), USP | 2.25 |
| Magnesium stearate | 3.0 |
| (b) Capsule |  |
| Compound X | 10.0 |
| Mannitol, USP | 488.5 |
| Croscarmellose sodium | 15.0 |
| Magnesium stearate | 1.5 |

The above formulations may be obtained by conventional procedures well known in the pharmaceutical art. The tablets may be enteric coated by conventional means, for example to provide a coating of cellulose acetate phthalate.

CHEMICAL FORMULAE

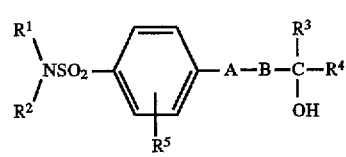

I

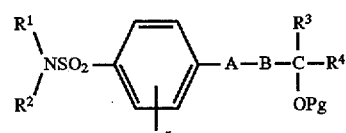

II

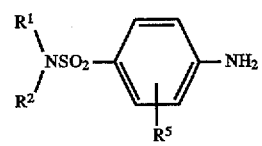

III

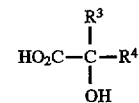

IV

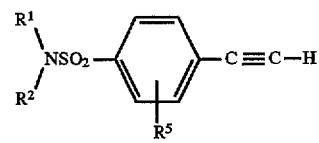

V

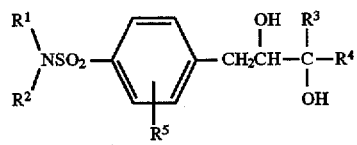

VI

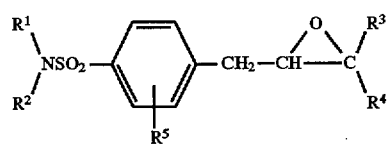

VII

VIII

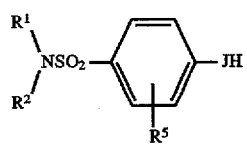

IX

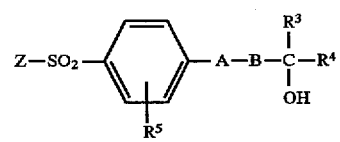

X

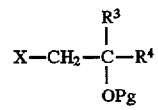

XI

19

-continued
CHEMICAL FORMULAE

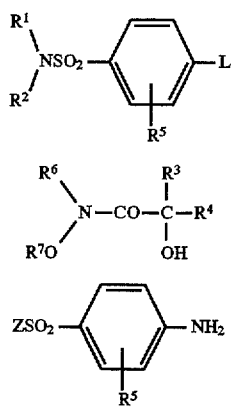

What is claimed is:

1. A compound of formula I:

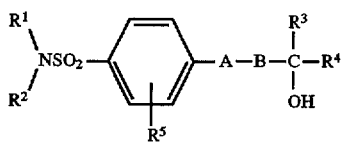

wherein, one of $R^1$ and $R^2$ is pyridyl and the other is selected from (1–3 C)alkyl, pyridyl and phenyl which phenyl is unsubstituted or substituted by one or two substituents selected independently from (1–4 C)alkyl, (1–4 C)alkoxy, (2–4 C)alkenyloxy, hydroxy, halo and cyano, or $R^1$ and $R^2$ together with the nitrogen atom to which they are attached form morpholino, thiomorpholino, piperidinyl, pyrrolidinyl or imidazolyl;

A-B is selected from NHCO, OCH$_2$, SCH$_2$, NHCH$_2$, trans-vinylene, and ethynylene;

$R^3$ and $R^4$ are independently (1–3 C)alkyl substituted by from 0 to 2 k+1 atoms selected from fluoro and chloro wherein k is the number of carbon atoms in the said (1–3 C)alkyl, provided that $R^3$ and $R^4$ are not both methyl; or $R^3$ and $R^4$, together with the carbon atom to which they are attached, form a 3–5 membered cycloalkyl ring optionally substituted by from 0 to 2 m-2 fluorine atoms wherein m is the number of carbon atoms in said ring; and $R^5$ is hydrogen, (1–4 C)alkyl, (1–4 C)haloalkyl, (1–4 C)alkoxy, (1–4)haloalkoxy, cyano, nitro, (2–4 C)alkenyloxy or trifluoromethylthio;

or a pharmaceutically acceptable in vivo hydrolyzable ester of said compound of formula I; or a pharmaceutically acceptable salt of said compound or said ester; provided the compound is not 3-hydroxy-3-methyl-1-(4-morpholinosulfonylphenyl)-4,4,4-trifluorobut-1-yne.

2. A compound as claimed in claim 1 wherein one of $R^1$ and $R^2$ is pyridyl and the other is selected from hydrogen, methyl, ethyl, propyl and phenyl, or $R^1$ and $R^2$ together with the nitrogen to which they are attached form morpholino, thiomorpholino, piperidinyl or pyrrolidinyl.

3. A compound as claimed in claim 1, wherein $R^5$ is hydrogen.

4. A compound as claimed in claim 1, wherein A-B is NHCO.

5. A compound as claimed in claim 1 which is selected from: 3,3,3-trifluoro-2-hydroxy-2-methyl-N-[4-(1-piperidinyl-sulfonyl)phenyl]propanamide; 3,3,3-trifluoro-2-trifluoro-2-hydroxy-2-methyl-N-[4-(1-pyrrolidinylsulfonyl) phenyl]propanamide; 3,3,3-trifluoro-2-hydroxy-2-methyl-N-[4-(morpholinosulfonyl)phenyl]propanamide; 3,3,3-trifluoro-2-hydroxy-2-methyl-N-[4-) thiomorpholinosulfonyl)phenyl]propanamide; 4,4,4-trifluoro-3-hydroxy-3-methyl-1-[4-(1-pyrrolidinylsulfonyl) phenyl]-but-1-yne; 4,4,4-trifluoro-3-hydroxy-3-methyl-1-[4-(1-pyrrolidinylsulfonyl)phenyl]-trans-but-1-ene; and 4,4,4-trifluoro-3-hydroxy-3-methyl-1-[4-(morpholinosulfonyl) phenyl]-trans-but-1-ene.

6. A compound as claimed in claim 1 which is selected from: 3,3,3-trifluoro-2-hydroxy-2-methyl-2-methyl-N-[4-(1-piperidinylsulfonyl)phenyl]propanamide; 3,3,3-trifluoro-2-hydroxy-2-methyl-N-[4-(1-pyrrolidinylsulfonyl)phenyl] propanamide; 3,3,3-trifluoro-2-hydroxy-2-methyl-N-[4-(morpholinosulfonyl)phenylphenyl]propanamide; and 3,3, 3-trifluoro-2-methyl-N-[4-(thiomorpholinosulfonyl)phenyl] propanamide.

7. A pharmaceutical composition comprising a compound of formula I:

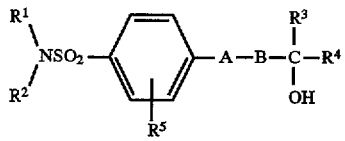

wherein either one of $R^1$ and $R^2$ is pyridyl and the other is selected from hydrogen, (1–3 C)alkyl, pyridyl and phenyl which phenyl is unsubstituted or substituted by one or two substituents selected independently from (1–4 C)alkyl, (1–4 C)alkoxy, (2–4 C)alkenyloxy, hydroxy, halo and cyano, or $R^1$ and $R^2$ together with the nitrogen atom to which they are attached form morpholino, thiomorpholino, piperidinyl, pyrrolidinyl or imidazolyl;

A-B is selected from NHCO, OCH$_2$, SCH$_2$, NHCH$_2$, trans-vinylene, and ethynylene;

$R^3$ and $R^4$ are independently (1–3 C)alkyl substituted by from 0 to 2 k+1 atoms selected from fluoro and chloro wherein k is the number of carbon atoms in the said (1–3 C)alkyl, provided that $R^3$ and $R^4$ are not both methyl; or $R^3$ and $R^4$, together with the carbon atom to which they are attached, form a 3–5 membered cycloalkyl ring optionally substituted by from 0 to 2 m-2 fluorine atoms wherein m is the number of carbon atoms in said ring; and $R^5$ is hydrogen, (1–4 C)alkyl, (1–4 C)haloalkyl, (1–4 C)alkoxy, (1–4)haloalkoxy, cyano, nitro, (2–4 C)alkenyloxy or trifluoromethylthio;

or a pharmaceutically acceptable in vivo hydrolyzable ester of said compound of formula I; or a pharmaceutically acceptable salt of said compound or said ester; and a pharmaceutically acceptable diluent or carrier;

provided the compound is not 3-hydroxy-3-methyl-1-(4-morpholinosulfonylphenyl)-4,4,4-trifluorobut-1-yne.

8. A method for the treatment of urinary incontinence, comprising administering to a mammal (including man) in need of such treatment an effective amount of a compound of formula I:

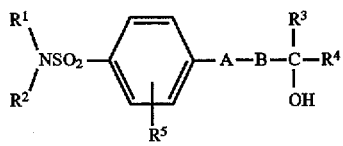

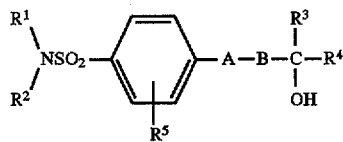

formula I:

wherein, one of R¹ and R² is pyridyl and the other is selected from hydrogen, (1–3 C)alkyl, pyridyl and phenyl which phenyl is unsubstituted or substituted by one or two substituents selected independently from (1–4 C)alkyl, (1–4 C)alkoxy, (2–4 C)alkenyloxy, hydroxy, halo and cyano, or R¹ and R² together with the nitrogen atom to which they are attached form morpholino, thiomorpholino, piperidinyl, pyrrolidinyl or imidazolyl;

A-B is selected from NHCO, OCH₂, SCH₂, NHCH₂, trans-vinylene, and ethynylene;

R³ and R⁴ are independently (1–3 C)alkyl substituted by from 0 to 2 k+1 atoms selected from fluoro and chloro wherein k is the number of carbon atoms in the said (1–3 C)alkyl, provided that R³ and R⁴ are not both methyl; or R³ and R⁴, together with the carbon atom to which they are attached, form a 3–5 membered cycloalkyl ring optionally substituted by from 0 to 2 m-2 fluorine atoms wherein m is the number of carbon atoms in said ring; and R⁵ is hydrogen, (1–4 C)alkyl, (1–4 C)haloalkyl, (1–4 C)alkoxy, (1–4)haloalkoxy, cyano, nitro, (2–4 C)alkenyloxy or trifluoromethylthio;

or a pharmaceutically acceptable in vivo hydrolyzable ester of said compound of formula I; or a pharmaceutically acceptable salt of said compound or said ester;

provided the compound is not 3-hydroxy-3-methyl-1-(4-morpholinosulfonylphenyl)4,4,4-trifluorobut-1-yne.

9. A method for relaxing bladder smooth muscle, comprising administering to a mammal (including man) in need of such treatment an effective amount of a compound of formula I:

wherein, one of R¹ and R² is pyridyl and the other is selected from hydrogen, (1–3 C)alkyl, pyridyl and phenyl which phenyl is unsubstituted or substituted by one or two substituents selected independently from (1–4 C)alkyl, (1–4 C)alkoxy, (2–4 C)alkenyloxy, hydroxy, halo and cyano, or R¹ and R² together with the nitrogen atom to which they are attached form morpholino, thiomorpholino, piperidinyl, pyrrolidinyl or imidazolyl;

A-B is selected from NHCO, OCH₂, SCH₂, NHCH₂, trans-vinylene, and ethynylene;

R³ and R⁴ are independently (1–3 C)alkyl substituted by from 0 to 2 k+1 atoms selected from fluoro and chloro wherein k is the number of carbon atoms in the said (1–3 C)alkyl, provided that R³ and R⁴ are not both methyl; or R³ and R⁴, together with the carbon atom to which they are attached, form a 3–5 membered cycloalkyl ring optionally substituted by from 0 to 2 m-2 fluorine atoms wherein m is the number of carbon atoms in said ring; and R⁵ is hydrogen, (1–4 C)alkyl, (1–4 C)haloalkyl, (1–4 C)alkoxy, (1–4)haloalkoxy, cyano, nitro, (2–4 C)alkenyloxy or trifluoromethylthio;

or a pharmaceutically acceptable in vivo hydrolyzable ester of said compound of formula I; or a pharmaceutically acceptable salt of said compound or said ester;

provided the compound is not 3-hydroxy-3-methyl-1-(4-morpholinosulfonylphenyl)-4,4,4-trifluorobut-1-yne.

* * * * *

UNITED STATES PATENT AND TRADEMARK OFFICE
CERTIFICATE OF CORRECTION

PATENT NO.    :    5,693,639

DATED         :    DECEMBER 2, 1997

INVENTOR(S)   :    EMPFIELD ET AL

It is certified that error appears in the above-identified patent and that said Letters Patent is hereby corrected as shown below:

Column 20, line 19, insert -- 2-hydroxy- -- between "3-trifluoro-" and "2-methyl".

Signed and Sealed this

Eighteenth Day of August, 1998

*Attest:*

BRUCE LEHMAN

*Attesting Officer*    *Commissioner of Patents and Trademarks*